United States Patent
Lacoste

(10) Patent No.: US 9,757,595 B2
(45) Date of Patent: Sep. 12, 2017

(54) SYSTEMS AND METHODS FOR SYNCHRONIZING ULTRASOUND TREATMENT OF THRYOID AND PARATHYROID WITH MOVEMENTS OF PATIENTS

(75) Inventor: Francois Lacoste, Paris (FR)

(73) Assignee: Theraclion SA, Malakoff (FR)

( * ) Notice: Subject to any disclaimer, the term of this patent is extended or adjusted under 35 U.S.C. 154(b) by 505 days.

(21) Appl. No.: 12/251,175

(22) Filed: Oct. 14, 2008

(65) Prior Publication Data

US 2010/0094177 A1 Apr. 15, 2010

(51) Int. Cl.
| | | |
|---|---|---|
| A61N 7/00 | (2006.01) | |
| A61N 7/02 | (2006.01) | |
| A61B 5/00 | (2006.01) | |
| A61B 17/00 | (2006.01) | |
| A61B 90/00 | (2016.01) | |

(52) U.S. Cl.
CPC .............. *A61N 7/02* (2013.01); *A61B 5/4205* (2013.01); *A61B 2017/00057* (2013.01); *A61B 2017/00694* (2013.01); *A61B 2090/064* (2016.02); *A61B 2090/378* (2016.02)

(58) Field of Classification Search
CPC A61B 2017/00057; A61B 2017/00694; A61B 2019/464; A61B 2019/5276; A61B 2090/064; A61B 2090/378; A61B 2018/00023; A61B 2018/00642; A61B 2090/061; A61B 2090/374; A61B 2090/376; A61B 90/36; A61N 7/02
USPC .......................................................... 601/3
See application file for complete search history.

(56) References Cited

U.S. PATENT DOCUMENTS

| | | |
|---|---|---|
| 5,419,327 A | 5/1995 | Rohwedder et al. |
| 5,720,286 A | 2/1998 | Chapelon |
| 5,949,080 A | 9/1999 | Ueda et al. |
| 6,076,005 A | 6/2000 | Sontag et al. |
| 6,097,984 A | 8/2000 | Douglas |
| 6,398,731 B1 | 6/2002 | Mumm et al. |

(Continued)

FOREIGN PATENT DOCUMENTS

| | | | |
|---|---|---|---|
| JP | WO 2006/013797 | * 9/2006 | ............... A61B 5/11 |
| WO | 2005/120373 | 12/2005 | |

(Continued)

OTHER PUBLICATIONS

Nederkoorn et al., Recording of Swallowing Events Using Electromyography as a Non-Invasive Measurement of Salivation, Appetite 1999, 33(3), pp. 361-369.

(Continued)

*Primary Examiner* — Amanda Lauritzen Moher
(74) *Attorney, Agent, or Firm* — Davis & Bujold PLLC; Michael J. Bujold

(57) ABSTRACT

A treatment device and methods for HIFU treatment of thyroid and parathyroid disorders are provided. The treatment device comprises the first sensor for detecting swallowing motion and the second sensor for tracking the motion of the thyroid and parathyroid tissue with ultrasound imaging. Thus, the treatment device allows for safe and non-invasive use of HIFU on thyroid and parathyroid tissue of patients by synchronizing HIFU pulse delivery with patient swallowing and/or directing the applicator of HIFU energy to follow the appropriate tissue when the patient moves.

6 Claims, 4 Drawing Sheets

(56) References Cited

U.S. PATENT DOCUMENTS

| | | | |
|---|---|---|---|
| 6,484,053 B2 | 11/2002 | Leelamanit et al. | |
| 6,488,626 B1 | 12/2002 | Lizzi et al. | |
| 6,517,492 B2 | 2/2003 | Koblanski | |
| RE38,030 E * | 3/2003 | Chapelon | A61B 8/12 600/439 |
| 6,618,132 B1 * | 9/2003 | Vann | 356/141.1 |
| 7,171,257 B2 | 1/2007 | Thomson | |
| 7,318,805 B2 | 1/2008 | Schweikard et al. | |
| 7,585,296 B2 | 9/2009 | Edwards | |
| 2001/0012387 A1 | 8/2001 | Polz | |
| 2002/0193685 A1 * | 12/2002 | Mate et al. | 600/424 |
| 2004/0015104 A1 | 1/2004 | Goldberger et al. | |
| 2004/0122311 A1 | 6/2004 | Cosman | |
| 2005/0027333 A1 | 2/2005 | Lennox | |
| 2005/0187495 A1 | 8/2005 | Quistgaard et al. | |
| 2006/0079764 A1 | 4/2006 | Wright et al. | |
| 2006/0100509 A1 | 5/2006 | Wright et al. | |
| 2006/0203615 A1 | 9/2006 | Gal et al. | |
| 2006/0217793 A1 | 9/2006 | Costello | |
| 2006/0241443 A1 | 10/2006 | Whitmore, III et al. | |
| 2006/0241446 A1 | 10/2006 | White et al. | |
| 2006/0254600 A1 * | 11/2006 | Danek et al. | 128/898 |
| 2006/0282010 A1 | 12/2006 | Martin et al. | |
| 2006/0293598 A1 * | 12/2006 | Fraser | 600/439 |
| 2007/0055155 A1 * | 3/2007 | Owen et al. | 600/439 |
| 2007/0129631 A1 | 6/2007 | Ma et al. | |
| 2007/0161894 A1 | 7/2007 | Zdeblick et al. | |
| 2007/0270687 A1 | 11/2007 | Gardi et al. | |
| 2007/0276244 A1 | 11/2007 | Sui | |
| 2008/0030457 A1 | 2/2008 | Schneider | |
| 2008/0269607 A1 | 10/2008 | Ishida et al. | |
| 2009/0030346 A1 * | 1/2009 | Kojima et al. | 600/590 |
| 2012/0238873 A1 * | 9/2012 | Lacoste | A61N 7/02 600/439 |
| 2013/0261368 A1 * | 10/2013 | Schwartz | A61N 5/1027 600/1 |
| 2016/0144147 A1 * | 5/2016 | Wolfram | A01N 1/0236 435/1.1 |

FOREIGN PATENT DOCUMENTS

| | | | |
|---|---|---|---|
| WO | 2006/129045 | 12/2006 | |
| WO | 2006/129047 | 12/2006 | |
| WO | WO 2006129099 A1 * | 12/2006 | A61M 37/0092 |

OTHER PUBLICATIONS

Wehrmann et al., Shock Wave Treatment of Salivary Duct Stones: Substantial Progress with a Minilithotripter, Clinical Investigator, 72, pp. 604-608, 1994.

Esnault et al., High Intensity Focused Ultrasound (HIFU) Ablation Therapy for Thyroid Nodules, Thyroid, Ultrasound and Ultrasound Guided FBA, pp. 219-236, Springer, May 2008.

* cited by examiner

SYSTEMS AND METHODS FOR SYNCHRONIZING ULTRASOUND TREATMENT OF THRYOID AND PARATHYROID WITH MOVEMENTS OF PATIENTS

FIELD OF THE INVENTION

The present invention is generally directed to devices and methods for synchronizing ultrasound therapy, and in some embodiments, High Intensity Focused Ultrasound (HIFU) pulse delivery, with movements of a patient undergoing treatment directed to thyroid and parathyroid tissue (for example). Such movements may include, for example, swallowing.

BACKGROUND OF THE INVENTION

The use of ultrasound, including high intensity focused ultrasound (HIFU) for therapeutic purposes has received significant attention in the medical community. During treatment, a portion of the mechanical energy from these high intensity sound waves is converted at the targeted location into thermal energy. The amount of thermal energy converted can be sufficiently intense to cauterize tissue, or to cause tissue necrosis (by inducing a temperature rise to beyond 70° C.). Importantly, the focal point of this energy deposition can be tightly controlled so as to obtain tissue necrosis in a small target area without damaging adjoining tissue. Thus, both benign and malignant tumors can be destroyed with HIFU without surgical exposure to the tumor site.

A particular advantage of HIFU therapy over certain traditional therapies is that HIFU is less invasive. Further advantages include reduced blood loss, reduced risk of infection, shorter hospital stays, and lower health care costs. HIFU has the potential to provide an additional treatment methodology consistent with this trend by offering a method of non-invasive surgery. For example, HIFU enables transcutaneous tumor treatment without making a single incision, thus avoiding blood loss and the risk of infection and with few side effects. Furthermore, HIFU therapy may be performed without the need for general anesthesia, thereby reducing surgical complications and cost. Most importantly, these treatments may be performed on an outpatient basis, further reducing health care cost, while increasing patient comfort.

The application of HIFU for the destruction of benign and malignant tumors in the neck area presents a relatively new direction in the field. Patients with thyroid and parathyroid tumors stand to benefit significantly from relatively non-invasive nature of HIFU. Further, among benign conditions of the neck area, thyroid nodules are frequently discovered during routine physical examination or during investigations for other purposes. Recently, systematic ultrasonographic exploration of a French large adult cohort indicated that 14.5% of subjects had nodular thyroid structures (Valeix et al. (2001), Ann Endocrinol (Paris) 62(6):499-506.) In the United States, 40% of the female population age 50 or older are presented with thyroid nodules at ultrasonography, and the prevalence of thyroid nodules increases throughout life. Patients presenting with such benign nodules are subject to long follow-up procedures and the best therapeutic strategy after the discovery of such nodules is still a matter of debate. Often, the goal of the physician becomes avoiding surgery and choosing among minimally invasive treatments which may be done in an ambulatory settings and result in fewer sides effects compared to surgery.

HIFU is a promising non-invasive procedure for treatment of the disorders of the neck tissue. However, the enduring problems of HIFU application remain in accurately assessing, targeting and monitoring ablated tissues during the therapeutic treatment. Specifically, application of HIFU to the wrong tissue in the neck of a patient can lead lower treatment efficacy and to various side effects, such as for example loss of voice, due to damaging the laryngeal nerves. Thus, in an attempt to circumvent the deficiencies in the art, there have been devices developed to attempt synchronization of HIFU energy with the movements of patients.

U.S. Reissued Pat. No. RE38,030 teaches a method of applying focused ultrasound to the thyroid of a patient. The method includes monitoring the movement of the patient during the focused ultrasound treatment, particularly at the trachea. Echo location is used to determine the position of a portion of the patient's body. If a change in position is detected, an alarm signal is triggered and the position of the therapy device is changed. Thereby, the therapy on the thyroid is continued as the focused ultrasound is kept targeted on the thyroid.

RE38,030 is understood not specifically to disclose, teach or suggest movements in relation to swallowing, nor is it understood to disclose, teach or suggest a separate sensor for the detection of movement of the larynx. Moreover, RE38,030 also appears not to specifically disclose, teach or suggest the stoppage of signal from the focused ultrasound therapy device in response to patient movement including swallowing.

U.S. Pat. No. 6,076,005 is understood to be directed toward gating of therapeutic energy including sonic energy based on the respiratory cycle of the patient. The patient's lungs are monitored to provide quasi-continuous measurements of the actions of the patient's lungs. However, U.S. Pat. No. 6,076,005 is understood not to disclose, teach or suggest movements in relation to swallowing, nor does it teach a separate sensor for the detection of movement of the larynx. Further, U.S. Pat. No. 6,076,005 is also understood not to disclose, teach or suggest the stoppage of signal from the focused ultrasound therapy device in response to patient movement including swallowing.

Thus, there is understood a general need in the art to provide HIFU devices capable to deliver therapeutic energy to the correct tissue i.e. the thyroid or parathyroid, despite the movement of the tissue of the neck due to patient's swallowing or other movement during treatment.

SUMMARY OF THE INVENTION

The foregoing and other features, aspects, and advantages of the present invention will be more apparent from the following detailed description, which illustrates exemplary embodiments of the present invention.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the drawings, subsequent detailed description and appended claims. In some embodiments, the invention provides an ultrasound therapeutic treatment device comprising a first sensor for detecting at least one of neck motion, throat/neck motion and swallowing motion in a subject; a second sensor for detecting a thyroid and/or parathyroid in the subject, a high intensity focused ultrasound (HIFU) pulse generator and controlling means for controlling the HIFU pulse generator based on signals from at least one of the first sensor and the second sensor.

In some embodiments, the treatment device may comprise a controlling means for controlling various aspects of the method and/or system/device, such means may include a micro processor or the equivalent thereof. In some embodiments, when the first sensor detects movement of a patient, the controlling means stops pulse generation from the HIFU pulse generator. Preferably the first sensor is positioned on the larynx of the patient. In some embodiments, when the second sensor detects a change in position of a tissue in the patient from a first position to a second position, the controlling means adjusts the HIFU generator such that at least one HIFU pulse is focused on the tissue in the second position. Preferably the tissue is parathyroid and/or thyroid tissue. Optionally the second sensor is an ultrasonic scanning probe.

In some embodiments, the first sensor is selected from the group consisting of a strain gauge, a laser to measure distance, an electromyography sensor, and a combination of any of the foregoing.

In some embodiments, a method for treating disorders of thyroid and/or parathyroid with HIFU in a subject in need thereof is provided and may comprise positioning a first sensor to detect at least one of neck motion, throat motion and swallowing motion in the subject; positioning a second sensor to detect a position of a thyroid and/or parathyroid in the subject; positioning a HIFU pulse generator to provide at least one HIFU pulse to the subject; and controlling the HIFU pulse generator to cease HIFU pulses upon the first sensor detecting motion. Preferably, the second sensor is positioned sagitally i.e. parallel to the neck of the patient.

In some embodiments, the above noted method may further comprise providing at least one of controlling means for controlling the HIFU pulse generator and synchronizing means for synchronizing a signal from at least one of the first sensor and the second sensor with the HIFU pulse generator.

The above-noted method may further comprise detecting a change in position of the parathyroid and/or thyroid from a first position to a second position and adjusting the HIFU generator such that at least one HIFU pulse is focused on the parathyroid and/or thyroid in the second position.

The above-noted method may further comprise selecting the first sensor from the group consisting of a strain gauge, a laser to measure distance, an electromyography sensor and a combination of any of the foregoing.

In some embodiments, the method relates to the disorders of the thyroid and parathyroid selected form the group consisting of thyroid nodules, hyperthyroidism, primary or secondary hyperparathyroidism, thyroid cancer, parathyroid cancer and any combination of the foregoing.

In some embodiments, an ultrasound therapeutic treatment device/system is provided which may include a first sensor for detecting at least one of neck motion, throat motion and swallowing motion in a subject; a second sensor for detecting a thyroid and/or parathyroid in the subject; a high intensity focused ultrasound pulse (HIFU) generator; a micro processor for controlling the HIFU pulse generator based on signals from at least one of the first sensor and the second sensor. According to this embodiment, when the first sensor detects motion, the controlling means stops pulse generation from the HIFU pulse generator.

The second sensor may be used to detect a change in position of the parathyroid and/or thyroid from a first position to a second position. In such embodiments, the controlling means adjusts the HIFU generator such that a HIFU pulse is focused on the parathyroid and/or thyroid in the second position.

In some embodiments, a method for treating disorders of thyroid and/or parathyroid with HIFU in a subject in need thereof is provided and may include positioning a first sensor to detect at least one of neck motion, throat motion and swallowing motion in the subject; positioning a second sensor to detect a position of a thyroid and/or parathyroid in the subject; providing a HIFU pulse generator to provide at least one HIFU pulse to the subject. Furthermore, at least one of controlling means for controlling the HIFU pulse generator and synchronizing means for synchronizing a signal from at least one of the first sensor and the second sensor with the HIFU pulse generator are provided which in turn control the HIFU pulse generator to cease HIFU pulses upon the first sensor detecting motion.

The above-noted method may relate to detecting a change in position of the parathyroid and/or thyroid from a first position to a second position and adjusting the HIFU generator such that at least one HIFU pulse is focused on the parathyroid and/or thyroid in the second position.

Moreover, the above-noted method may relate to disorders of the thyroid and parathyroid selected form the group consisting of thyroid nodules, hyperthyroidism, primary or secondary hyperparathyroidism, thyroid cancer, parathyroid cancer and any combination of the foregoing.

In some embodiments, methods of the present invention may be used to treat and/or alleviate the symptoms of thyroid nodules, hyperthyroidism, primary or secondary hyperparathyroidism, thyroid cancer or parathyroid cancer and other known thyroid and parathyroid disorders.

Other objectives and advantages of the present invention will become obvious to the reader and it is intended that these objectives and advantages are within the scope of the present invention.

To accomplish the above and related objectives, this invention may be embodied in the form illustrated in the accompanying drawings, attention being called to the fact, however, that the drawings are illustrative only, and that changes may be made in the specific construction illustrated.

BRIEF DESCRIPTION OF THE DRAWINGS

For a better understanding of the present invention, reference is made to the following description, taken in conjunction with the accompanying drawings, in which like reference characters refer to like parts throughout, and in which.

DETAILED DESCRIPTION

Figure 1:
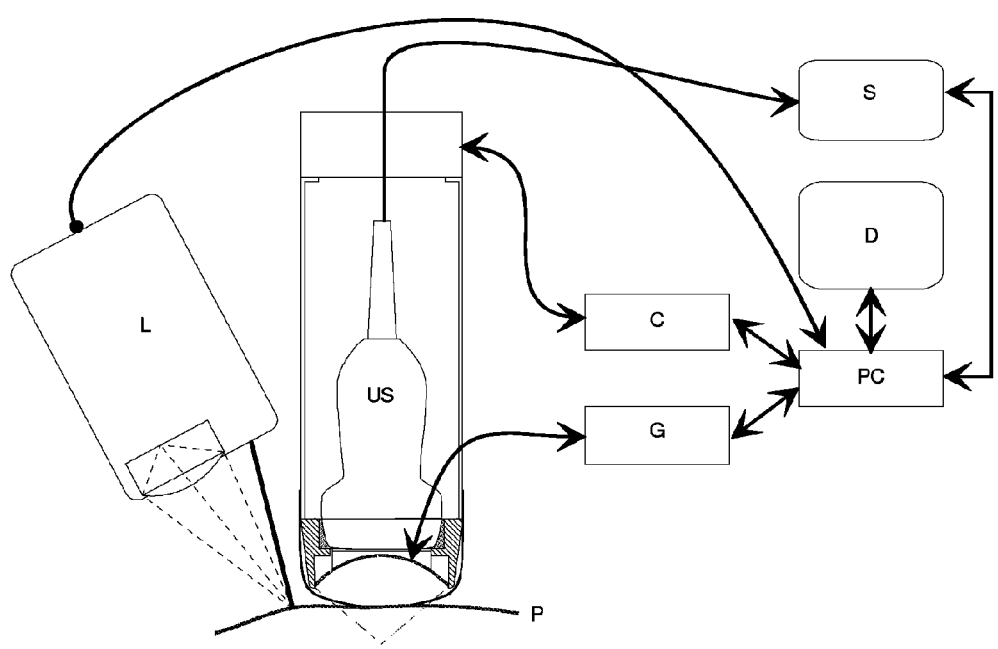
FIG. 1 is an overall diagrammatic view of a complete treatment device that is suitable for incorporating the first and second sensors of the invention according to some embodiments.

It is noted that in this disclosure and particularly in the claims and/or paragraphs, terms such as "comprises," "comprised," "comprising," and the like can have the meaning attributed to it in U.S. patent law; that is, they can mean "includes," "included," "including," and the like, and allow for elements not explicitly recited. These and other embodiments are disclosed or are apparent from and encompassed by, the following description.

The terms "HIFU pulse generator," as used herein and in the claims that follow all refer to a HIFU transducer that is capable of being energized to produce ultrasonic waves that are much more energetic than the ultrasonic pulses produced by an imaging transducer, and which can be focused or directed onto a discrete location, such as a treatment site in a target area.

In this respect, before detailing at least one embodiment of the invention, it is to be understood that the invention is not limited in its application to the details of construction and to the arrangements of the components set forth in the following description or illustrated in the drawings. The invention is capable of other embodiments and of being practiced and carried out in various ways where particular configurations, process steps, and materials disclosed herein as such configurations, process steps, and materials may vary somewhat. In addition, it is to be understood that the phraseology and terminology employed herein are for the purpose of the description and should not be regarded as limiting. Furthermore, as will be apparent to those skilled in the art, the present invention may be embodied in other specific forms without departing from the essential characteristics thereof.

For purposes of the description of the drawings and the embodiments of the present invention, as mentioned for the drawing, FIG. 1 may not be drawn to scale. Some areas drawn may be larger and/or simpler in order to clearly portray the improvement to what has already been established. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed. It is also to be understood that the terminology employed herein is used for the purpose of describing particular embodiments only and is not intended to be limiting since the scope of the present invention will be limited only by the appended claims and equivalents thereof.

Referring now in detail to the drawing, the first and second sensor according to some embodiments of the present invention can be incorporated in a treatment device as shown diagrammatically in FIG. 1. According to this device, the sensors "L" and "US" are associated with a plurality of elements such as, for example, a power generator "G", for powering the treatment means, a displacement controller "C", for displacing the head, an ultrasound scanner "S", connected to the probe, a display screen "D", and a computer "PC" that serves to manage the device. All of the elements of the device including sensors "L" and "US" are connected to the "PC". The elements "US", "G", "C", "PC" "D" and others, are described in detail in related applications WO 2006/129047 and WO 2006/129045 incorporated by reference herein.

The first sensor may be a non contact distance measuring tool "L", such as for example a laser. This is depicted on the left side of the FIG. 1. The way "L" detects motion may be as follows: "L" emits a laser beam which is directed towards the throat of the patient. In other embodiments, the first sensor is placed directly on the patient's larynx.

The light reflected by the patient skin is focused by the lens onto a linear detector (the light follows the dashed lines as shown in FIG. 1). Depending on the position of the focused light on the linear detector, the distance of the skin is calculated. "L" can be a commercial device, such as Model OADM 20I4471/S14C from Baumer Electric.

The OADM laser distance sensor may be a self-contained unit designed to accurately measure the distance to a target based on triangulation principal and output the measurement either through an analog and/or a digital interface. The sensors preferably incorporate microprocessor technology to further optimize the dual analog output. The OADM 20 laser distance sensors may utilize a fast microcontroller that enables flexible adaptation of different parameters to the user's requirements. Laser light is available in either a laser beam or a laser beam line configuration depending on the target's surface. These sensors may be equipped with a 90° connector for quick and easy adaptability to the application environment.

In some embodiments, the first sensor may be a strain gauge, and/or may be or include an electromyography sensor.

The second sensor is mostly used to track the motion of the tissues, such as for example thyroid and/or parathyroid with ultrasound imaging. In one embodiment, the imaging means may be ultrasonic imaging probe, in another embodiment, the imaging means may be X-ray probe, and in yet another embodiment, the imaging means may be a Magnetic Resonance Imaging (MRI) device. In another embodiment, the second sensor is an ultrasonic scanning probe. The imaging means achieve representation of the tissue motion in space or in a plane. It is advantageous that the ultrasound array is disposed sagittal to the patient, i.e. parallel to the neck The preferred imaging means according to the instant invention is the ultrasonic probe as designated by "US". This element of the therapeutic device is shown in FIG. 1 and is described in detail in the related applications WO 2006/129045 and WO 2006/129047 which are incorporated by reference herein.

In some embodiments, the synchronizing electronics may be embedded in a computer, "PC" as shown in FIG. 1. The synchronizing electronics may combine the signals from the swallowing sensor with HIFU pulse triggers, such that if swallowing is detected, no pulse is triggered; and/or directing the applicator of HIFU energy to follow the appropriate tissue when the patient moves.

Embodiments of the disclosure provides methods for administering HIFU therapy to treat disorders of thyroid and parathyroid tissue. These include treatment of the benign and malignant thyroid and parathyroid disorders such as for example thyroid nodules, hyperthyroidism, primary and secondary hyperparathyroidism, thyroid and parathyroid cancer and others.

In general, the treatment of the thyroid and parathyroid tissue with an HIFU device takes 10 to 30 minutes in an outpatient clinic. A local anesthetic is administered prior to treatment. The ultrasound energy may be gradually increased until more than 70% of the targeted thyroid or parathyroid tissue is destroyed.

It has been observed that a complete thyroid and/or parathyroid tumor treatment (100% shrinkage) may be obtained. Alternatively, the tumor may be treated in several sessions, with sufficient time between each session for the macrophages in the patient's body to clear away the necrotic tissue resulting from the previous treatment session, thus effectively debriding the treatment side and exposing remaining tumor tissue for the next HIFU therapy session. Several HIFU therapy sessions may be needed to completely eradicate the tumor. Further, the treatment of a benign and/or malignant tumor using a combination of HIFU and drugs, such as for example thyrotropin (TSH) suppressive levothyroxine (LT4) and/or standard chemotherapy drugs, may yield synergistic results, particularly by beginning the HIFU therapy after the maximum benefit of the drug therapy on the tumor and/or nodule has been realized.

Figure 2:
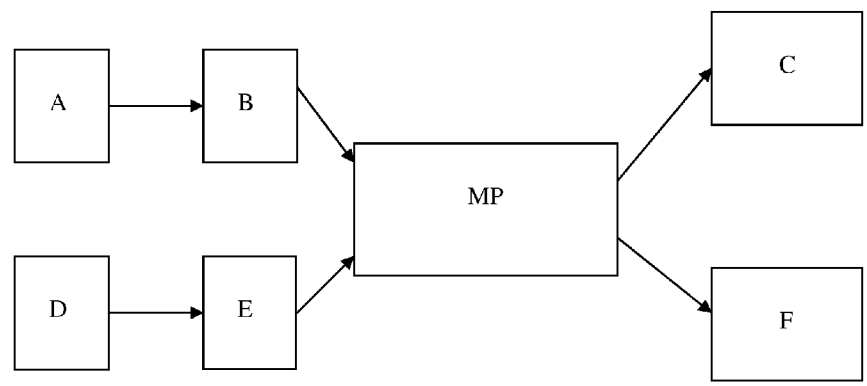
FIG. 2 and FIG. 3 are a flow charts showing the various steps of a method for treating disorders of thyroid and/or parathyroid with HIFU in a subject in need thereof according to some embodiments.

As shown in FIG. 2, when performing the treatment according to the instant method, the subject receiving the treatment periodically swallows (A). Accordingly, the first sensor, which is placed directly on the larynx, may be used to detect such movement (e.g., swallowing) of the subject (B) and then may transmit a signal to the microprocessor (MP) regarding such detected motion. The microprocessor may then signal for the HIFU generator to stop generating pulses during the period of the motion, thereby preventing injury to the subject receiving treatment (C). Concurrently, the subject receiving treatment periodically moves the neck region of the subject undergoing treatment (D). Accordingly, in some embodiments, the second sensor may be used to detect such movement of the subject with the use of imaging means, from a first position to a second position (E), and then transmits a signal regarding this movement to the microprocessor (MP). The microprocessor may then signal the controller (e.g., a microprocessor) of the HIFU generator to reposition the generator to keep the HIFU pulses focused on the thyroid and/or parathyroid of the subject in the second position (F).

Figure 3:
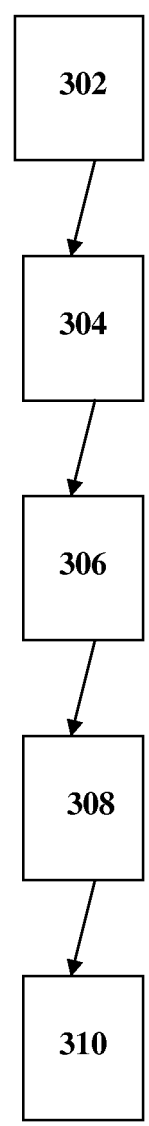

The flow chart shown in FIG. 3 is a diagram outlining the various steps of the method for treating disorders of thyroid and/or parathyroid with HIFU in a subject in need thereof according to some embodiments of the disclosure. Starting at 302, the first sensor is positioned to detect at least one of neck motion, throat motion and swallowing motion. In some embodiments of the instant method, the first sensor is placed directly on the larynx. Then at 304, the second sensor is positioned to detect position of a thyroid and/or parathyroid in the subject. In some embodiments of the instant method, the second sensor is positioned directly on thyroid and/or parathyroid tissue. At 306, the HIFU pulse generator is provided to generate at least one HIFU pulse to the subject. At 308, the controlling means for controlling the HIFU pulse generator are provided. In some embodiments, in addition to controlling means, synchronizing means for synchronizing a signal from at least one of the first sensor and the second sensor with the HIFU pulse generator are provided. Finally at 310, the controlling HIFU generator ceases the HIFU pulses upon the first sensor detecting motion. The synchronizing means may comprise a microprocessor and/or other electronic or software run on a microprocessor (e.g., computer), and may be combined with a microprocessor/computer which comprises the controlling means.

Figure 4:
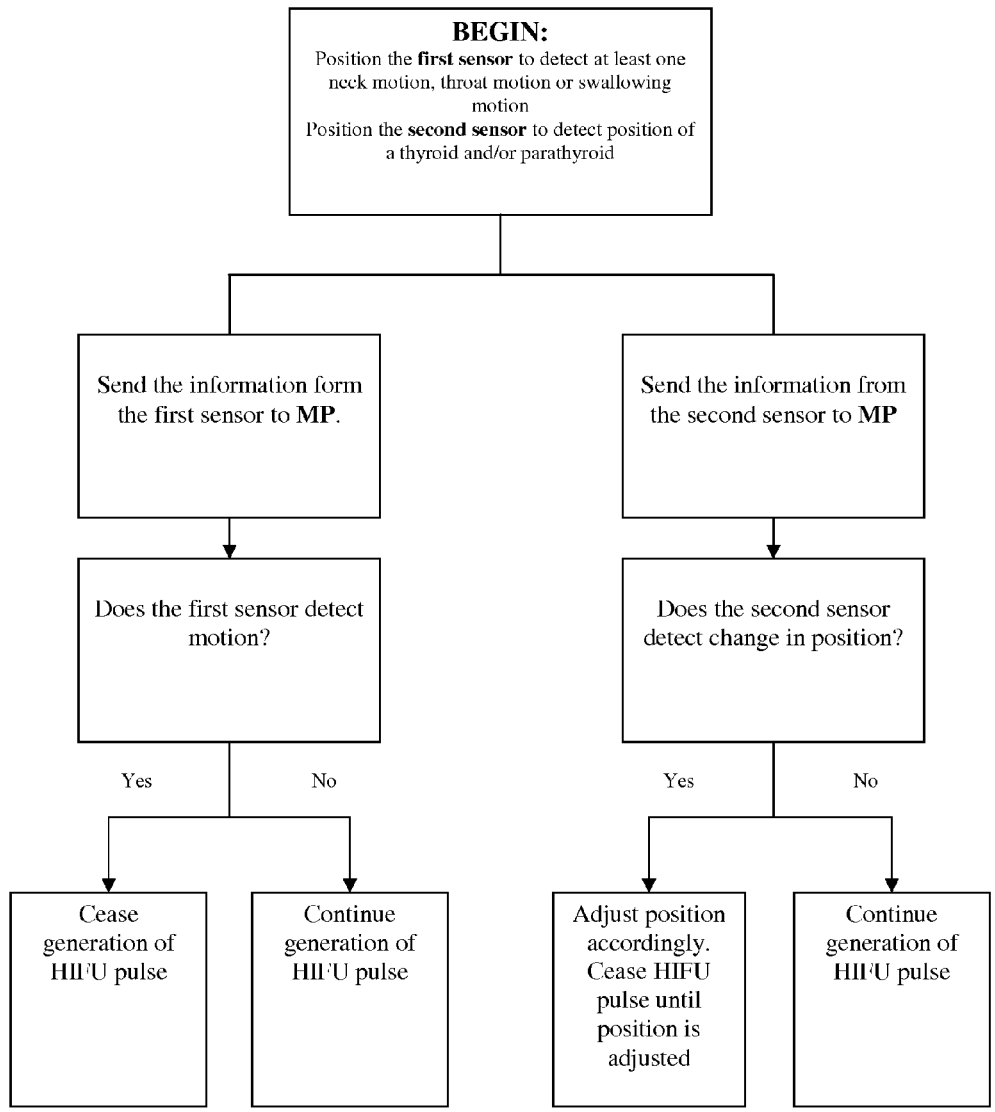
FIG. 4 is a flow chart illustrating steps (for some method embodiments of the present disclosure) followed during use of some apparatus/system embodiments disclosed in the present disclosure.

The MP unit controls and, in some embodiments also synchronizes, a signal from at least one of the first sensor and the second senor with the HIFU pulse generator. Specifically, when first sensor detects at least one of neck motion, throat motion and swallowing motion, it sends a signal to the MP which processes information and in turn sends a signal to HIFU generator to cease HIFU pulses. Similarly, when the second sensor detects the change in position of the thyroid and parathyroid from first position to a second position, it sends a signal to the MP which processes information and in turn sends a signal to the HIFU pulse generator to adjust accordingly, such that for example, at least one HIFU pulse is focused on the parathyroid or thyroid in the second position. Some such embodiments are also summarized in FIG. 4. Specifically, the procedure begins by placing the first sensor to the neck area to detect at least one motion of the neck, throat and/or swallowing motion. If any motion is detected by the first sensor, the signal is send to the MP unit which processes the received information, and further sends the signal to the HIFU generator to cease HIFU pulse. If the first sensor does not detect any motion in the neck area, the signal is send to the MP unit which processes information and further sends the signal to HIFU generator to continue generating at least one pulse.

Similarly, if the second sensor detects a change in the position of the thyroid or parathyroid tissue, the signal is send to the MP which processes the information and further sends the signal to the HIFU generator to cease pulse until the position is adjusted such that the HIFU generator is focused on the thyroid or parathyroid tissue. However, if the second sensor does not detect position of the thyroid or parathyroid, the signal is send to the MP which further sends the signal to the HIFU generator to continue generating at least one pulse. In some embodiments, the signal received from the first sensor and the second sensor is send to the MP and further synchronized with the HIFU pulse generator.

While illustrative embodiments of the invention have been described above, it is, of course, understood that various modifications will be apparent to those of ordinary skill in the art. Such modifications are within the spirit and scope of the invention, which is limited and defined only by the appended claims.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

What is claimed is:

1. An ultrasound therapeutic treatment device comprising:
   a first sensor, coupled to a microprocessor, for detecting a source of a movement of at least one of a thyroid and a parathyroid in a patient undergoing treatment, and said source being in the form of at least one of neck motion, throat motion and swallowing motion of the patient undergoing treatment;
   a second sensor, coupled to the microprocessor, for detecting a location of the at least one of the thyroid and the parathyroid of the patient undergoing treatment;
   a high intensity focused ultrasound (HIFU) pulse generator, coupled to and controlled by the microprocessor, for generating treating ultrasound (HIFU) pulses directed at treating the at least one of the thyroid and the parathyroid of the patient undergoing treatment;
   the microprocessor controlling the HIFU pulse generator based on signals received from both the first sensor and the second sensor,
   wherein said first sensor is a non-contacting laser for measuring a distance and detecting the at least one of the neck motion, the throat motion and the swallowing motion of the patient undergoing treatment, and
   during treatment of the patient undergoing treatment, the microprocessor causes the HIFU pulse generator to generate the treating ultrasound pulses for treating the at least one of the thyroid and the parathyroid of the patient undergoing treatment, but when said first sensor detects the at least one of the neck motion, the throat motion and the swallowing motion of the patient undergoing treatment, the microprocessor temporarily interrupts the generation of the treating ultrasound (HIFU) pulses by the HIFU pulse generator during the at least one of the throat motion, the neck motion and the swallowing motion, and, following termination of the at least one of the neck motion, the throat motion and the swallowing motion of the patient undergoing treatment, the microprocessor causing the HIFU pulse generator to again generate the treating ultrasound (HIFU) pulses for treating the at least one of the thyroid and the parathyroid of the patient undergoing treatment.

2. The treatment device according to claim 1, wherein when the second sensor detects a change in position of the at least one of the parathyroid and the thyroid from a first position to a second position, the microprocessor adjusts the HIFU pulse generator such that at least one of the treating ultrasound (HIFU) pulses is focused on the at least one of the parathyroid and the thyroid in the second position.

3. A method for treating disorders of at least one of a thyroid and a parathyroid with a high intensity focused ultrasound (HIFU) in a subject in need thereof, the method comprising:
positioning a first sensor, coupled to a microprocessor, which is a non-contacting laser to measure distance, to detect a source of a movement of the at least one of the thyroid and the parathyroid in the subject undergoing treatment in the form of at least one of neck motion, throat motion and swallowing motion in the subject;
positioning a second sensor, coupled to the microprocessor, to detect a position of the at least one of the thyroid and the parathyroid in the subject;
positioning a high intensity focused ultrasound (HIFU) pulse generator, coupled to and controlled by the microprocessor, to generate at least one treating ultrasound (HIFU) pulse to the at least one of the thyroid and the parathyroid of the subject undergoing treatment;
controlling the HIFU pulse generator, with the microprocessor based on signals received from both the first sensor and the second sensor; and
controlling the HIFU pulse generator, with the microprocessor, to cease temporarily the treating ultrasound (HIFU pulses upon the first sensor detecting the at least one of the neck motion, the throat motion and the swallowing motion and to again automatically generate the treating ultrasound (HIFU) pulses upon termination of the at least one of the neck motion, the throat motion and the swallowing motion.

4. The method according to claim 3, further comprising:
using the microprocessor to control the HIFU pulse generator and synchronizing electronics for synchronizing the signals from at least one of the first sensor and the second sensor with the HIFU pulse generator.

5. The method according to claim 4, further comprising:
detecting a change in the position of the at least one of the parathyroid and the thyroid from a first position to a second position; and
adjusting the HIFU pulse generator such that at least one of the treating ultrasound (HIFU) pulses is focused on the at least one of the parathyroid and the thyroid in the second position.

6. The method according to claim 4, wherein disorders of the thyroid and the parathyroid are selected from the group consisting of: thyroid nodules, hyperthyroidism, primary or secondary hyperparathyroidism, thyroid cancer, parathyroid cancer and combinations thereof.

* * * * *